United States Patent [19]

Brunner et al.

[11] 4,454,772

[45] * Jun. 19, 1984

[54] METHOD FOR SAMPLING A FLUID FROM A WELL

[75] Inventors: Paul J. Brunner, Spring, Tex.; Charles A. Christopher, Broken Arrow, Okla.; Robert G. Pindell, Houston, Tex.

[73] Assignee: Texaco Inc., White Plains, N.Y.

[*] Notice: The portion of the term of this patent subsequent to Jun. 19, 2001 has been disclaimed.

[21] Appl. No.: 319,007

[22] Filed: Nov. 6, 1981

[51] Int. Cl.³ .............................................. G01N 1/10
[52] U.S. Cl. .............................. 73/863.31; 73/863.86; 141/236
[58] Field of Search ........... 73/863.31, 863.33, 863.02, 73/863.03, 864.04, 863.81, 863.86; 141/236, 35, 192, 244

[56] References Cited

U.S. PATENT DOCUMENTS

| | | | |
|---|---|---|---|
| 2,667,223 | 1/1954 | Farris | 166/19 |
| 2,728,397 | 12/1955 | Ruska | 166/64 |
| 2,927,641 | 3/1960 | Buck | 166/64 |
| 3,036,229 | 5/1962 | Kemp et al. | 73/863.33 |
| 3,045,750 | 7/1962 | Peters et al. | 166/52 |
| 3,362,222 | 1/1968 | Johnson et al. | 73/864.52 |
| 4,059,149 | 11/1977 | Harrison | 166/64 |

FOREIGN PATENT DOCUMENTS 0917080 1/1963 United Kingdom ............. 73/864.34

Primary Examiner—S. Clement Swisher
Attorney, Agent, or Firm—Robert A. Kulason; Jack H. Park; Henry C. Dearborn

[57] ABSTRACT

A method for sampling a fluid, as a multi-phase chemical product as liquid chemical tracers from a well in a field of wells comprising basically (1) injecting a sample of the liquid from the well through a plurality of valves, as solenoid valves on a plurality of liquid containers, and (2) controlling the well liquids responsive to a timing switch, as a stepping switch, through the valves into the liquid sample containers to be filled one after another, periodically, and consecutively from the well in a prearranged order for providing an improved method that is more accurate and more precise.

2 Claims, 4 Drawing Figures

METHOD FOR SAMPLING A FLUID FROM A WELL

BACKGROUND OF THE INVENTION

Previous to this invention, to get a fluid sample a person was required to go to the wellhead and wait the required period of time between samples before getting a meaningful or desired sample of well fluid, as a two-phase fluid. This was very time consuming, costly, and unreliable in that exact timing was difficult to achieve among other problems. These problems prompted the design of the disclosed method for sampling a liquid from a well that will automatically capture for analysis produced well fluid, as oil for example, at specific time intervals, for detection of injected chemical solutions, for example, for indicating the arrival of the multi-phase well fluid containing one or more chemical species, as polymers, surfactants, tracers, or treating chemicals at the well. The oil samples may likewise be analyzed for the presence of surfactants. Thus, the disclosed sampler more accurately measures each fluid sample for conservation of well fluid and thus requiring discharge of less waste oil that damages the environment from the single well. Particularly, the time of arrival and the time variation of concentration of the injected chemical solution at the producing well may be determined.

OBJECTS OF THE INVENTION

A primary object of this invention is to provide a new method for obtaining a plurality of fluid samples from a fluid source, in a plurality of sample containers to be filled, respectively, one after another, periodically, from the fluid source.

Another object of this invention is to provide an improved method for obtaining samples of well fluid, particularly a multi-phase fluid product containing chemical species from a well, that is more accurate and more precise.

A further object of this invention is to provide a new method for obtaining samples of well fluid from the well in a different prearranged order other than numerical consecutive order for security purposes.

A still further object of this invention is to provide a method for sampling fluid from a well that is easy to operate, comprises simple steps, is economical to carry out, and is of greater efficiency for the collection of samples of the well fluid.

Other objects and various advantages of the disclosed method for sampling fluid from a well will be apparent from the following detailed description, together with the accompanying drawings, submitted for purposes of illustration only and not intended to define the scope of the invention, reference being made for that purpose to the subjoined claims.

BRIEF DESCRIPTION OF THE DRAWINGS

The drawings diagrammatically illustrate by way of example, not by way of limitation, one form of the invention wherein like reference numerals designate corresponding parts in the several views in which.

Figure 4:
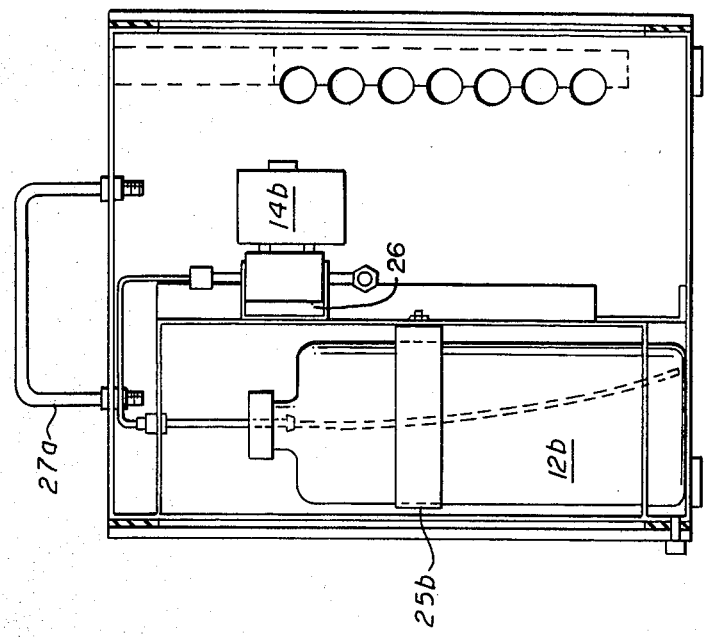
FIG. 4 is a sectional view taken at 4—4 on FIG. 2

The invention disclosed herein, the scope of which being defined in the appended claims is not limited in its application to the details of construction and arrangement of parts shown and described, since the invention is capable of other embodiments and of being practiced or carried out in various other ways. Also, it is to be understood that the phraseology or terminology employed here is for the purpose of description and not of limitation. Further, many modifications and variations of the invention as hereinbefore set forth will occur to those skilled in the art. Therefore, all such modifications and variations which are within the spirit and scope of the invention herein are included and only such limitations should be imposed as are indicated in the appended claims.

DESCRIPTION OF THE INVENTION

This invention comprising a method for obtaining samples of well fluid, particularly a multi-phase fluid product containing chemical species from a well, as produced oil-water well fluid, for example, for determining the specific time of arrival of injected chemical solutions at a producing well from an injection well.

A mechanism for practicing the above method is disclosed after the description of these methods.

Basically, the method for sampling fluids from a fluid source such as a well or a supply line, comprises, (1) injecting the sample fluid from the fluid source (21) through a plurality of valves (14a–14f) on a plurality of fluid sample containers (12a–12f), and (2) controlling the flow of the fluids, responsive to a timing switch means (16) through the valves into the fluid sample containers to be filled, consecutively, one after another, from the one fluid source, for providing an improved method that is more accurate and more precise.

As applied to a producing well as a source of fluid, another basic method may be (1) injecting the fluid from the well (21) into a plurality of sample container means (12a–12f), each container means having an inlet valve (14a–14f), and (2) controlling the flow of the well fluid from the well through the valves responsive to a switch means (16) into the fluid sample containers to be filled consecutively, one after another, and periodically, at predetermined periods of time, for improved accuracy and precision of operation of the fluid sampling.

For greater details, the first step in the above two methods may compromise:

(1) flowing a multi-phase fluid product repeatedly from the fluid source or injection well (21) into the fluid sample containers (12a–12f) for detecting the change with time of the chemical concentrations of the flowing multi-phase fluid product after arriving at the producing well from an injection well whereby analysis of the sample provides reservoir description.

Or the first step of the above two basic methods may comprise:

(1) flowing multi-phase fluid from the fluid source or producing well (21) through a plurality of solenoid valves (14a–14f) on the plurality of fluid sample containers (12a–12f) for detecting the change with time of the chemical concentrations of the flowing multi-phase chemical product after arriving at the producing well from an injection well.

The above multi-phase fluid method may be recited in greater detail by adding step (2) thus, (2) controlling the flow of the multi-phase well fluid through the solenoid valves (14a-14f) into the fluid sample containers (12a-12f), responsive to a stepping switch means (16), to be filled in consecutive order and periodically for predetermined periods of time from the well providing an improved method for sampling well fluids that is more accurate and more precise.

Likewise, the above second step may be modified comprising:

(2) controlling the flow of well fluid through the valves (14a-14f) into the fluid sample containers (12a-12f) responsive to an electrical timing means (16) for controlling the selection of different sample containers in consecutive order, one after another, to be filled periodically, for predetermined precise periods of time, from the well.

In addition, the second step may be modified as follows:

(2) injecting the multi-phase fluid from the fluid source of injection well (21) from the solenoid valves (14a-14f) responsive to the stepping switch means (16) into different sample containers (12b, 12d, 12a, etc.) periodically, from the well in a different prearranged order other than numerical consecutive order for security purposes.

DESCRIPTION OF A SAMPLER FOR CARRYING OUT THE ABOVE METHODS

One mechanism for practicing the method of the invention is set forth in the co-pending patent application, Ser. No. 319,005, filed on Nov. 6, 1981.

While various devices may be utilized for carrying out or practicing the inventive methods of the above identified patent application, FIGS. 1-4 illustrate at least one, inventive apparatus for practicing the methods described above.

Figure 1:
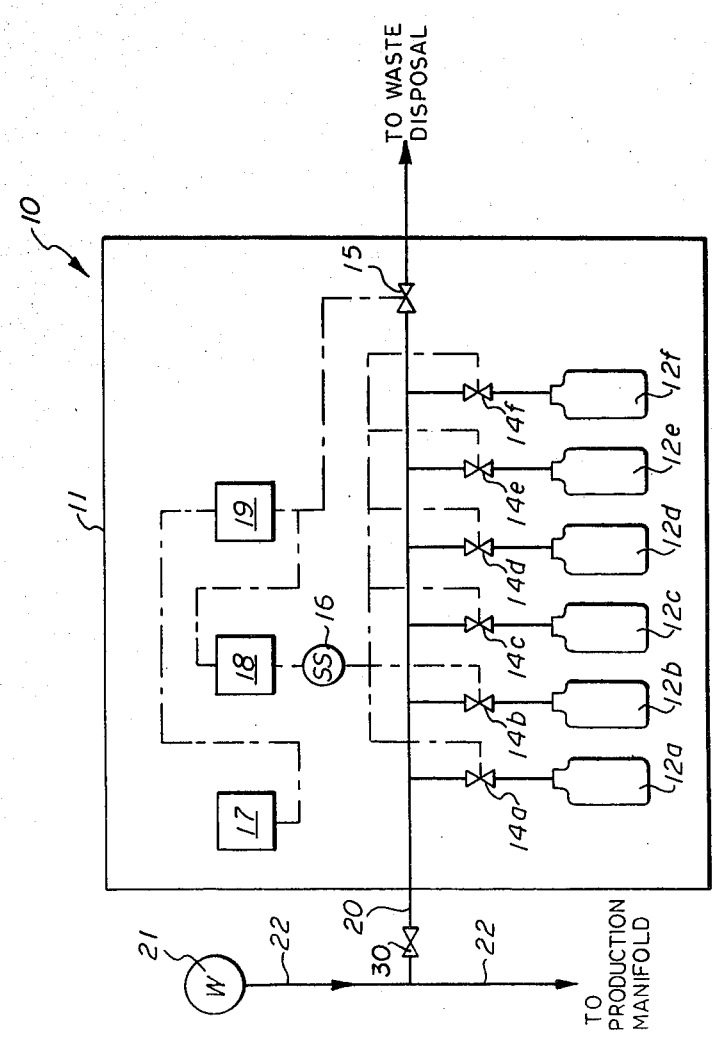
FIG. 1 is a schematic diagrammatic plan view of the time interval automatic well fluid sampler for sampling one well at a time, continuously, one of a field of oil wells.

FIG. 1 discloses a schematic diagrammatic plan view of the time interval automatic well fluid sampler 10 for taking fluid samples from any one of a plurality of wells. While this sampler has many uses, it is designed particularly for detecting the precise time of arrival of an injected chemical solution in a particular producing well from an injection well of a field of wells, for example, and/or the precise time of arrival of particular concentrations thereof thereafter.

Figure 2:
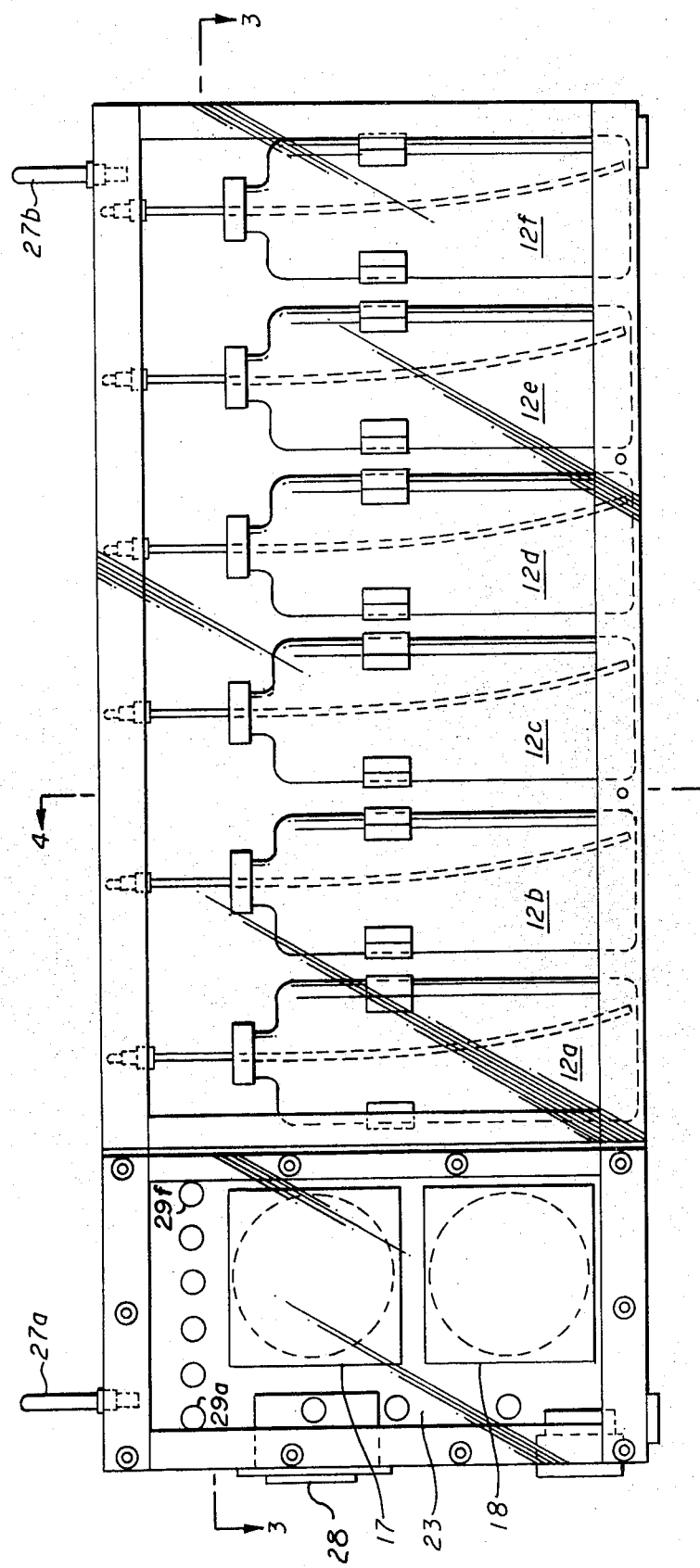
FIG. 2 is a schematic diagrammatic vertical sectional view of the time interval automatic well fluid sampler for sampling one well at a time, continuously, of a field of oil wells.
Figure 3:
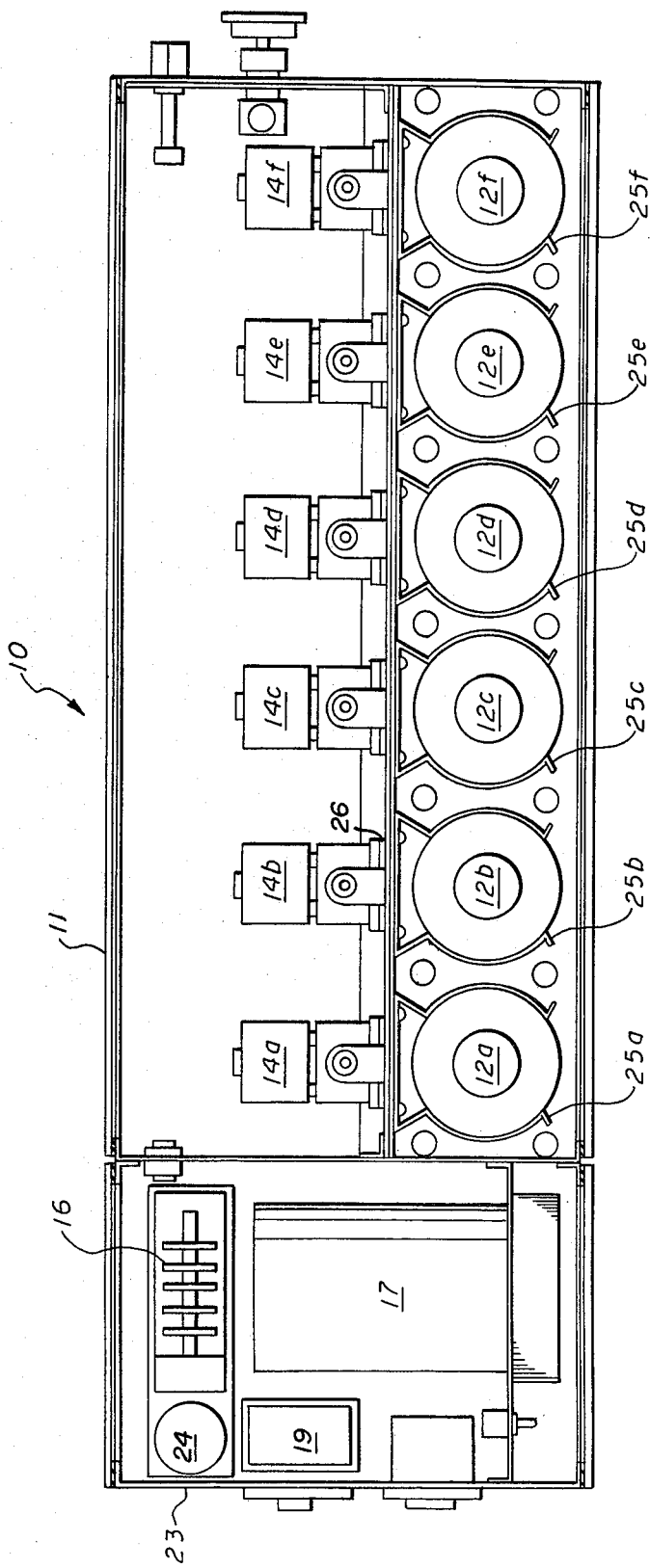
FIG. 3 is a sectional view taken at 3—3 on FIG. 2.

FIGS. 2-4 are enlarged views of the sampler 10.

Sampler 10 illustrated in FIGS. 1-4, comprises a housing 11 enclosing six (6) sample bottles 12a, 12b, 12c, 12d, 12e, and 12f, FIG. 2, and an inlet solenoid valve 14a-14f, FIG. 1 on each of the bottles for controlling its respective valve on each bottle supplied from supply and exhaust line 20. A pressure regulator valve 30 on line 20 always maintains the well fluid entering the sampler at a constant pressure and volume. Another solenoid valve 15 on line 20 purges the piping system of previous fluid prior to sampling. A stepping switch 16 in the electrical control panel box 23, FIG. 2, operates each of the valves in the order desired, as in numerical sequence from one well when awaiting the arrival of an injected chemical tracer or solution, for example, and then after it arrives, determination of the arrival time of the various concentrations may be required from each sample taken thereafter.

Three timers are utilized for controlling the flow of well fluid, electronic interval timer 17, FIG. 1, electronic sampler timer 18, and time delay relay purging timer 19.

Interval timer 17, FIG. 1, controls the time between samples by controlling each respective inlet valve 14a to 14f.

With pressure regulator valve 30 always insuring a constant pressure fluid to the valves, sampler timer 18, FIG. 1, controls each respective inlet valve 14a to 14f for filling its sample bottle 12a to 12f, respectively, exactly with a predetermined amount of well fluid. This is an important feature of the invention. In that respect, if the sample fluids have to be discarded, having a sample only large enough for testing with no extra amount to dispose of means the sample is easier to discard with less pollution of the environment.

Purging timer 19, FIG. 1, controls the main supply and exhaust line 20 from the well 21 which supplies oil to the production manifold 22. Thus, timer 19 purges the main exhaust line 20 by a precise predetermined amount just prior to filling of the next bottle.

FIGS. 2-4 provide more details of the time interval automatic well fluid sampler 10.

FIG. 2, a vertical sectional view of the sampler 10 shows at least two bottles 12b and 12c for receiving a sample each of the well fluid from the one well 21, FIG. 1, and two of the timers, interval timer 17, FIG. 2, and sample timer 18. All conventional electrical wiring between the timers and solenoid valves to permit them to operate as described above is deleted on this FIG. 2 for clarity of disclosure. Example interval timers may be ones set for intervals of 0.1 to 999.9 seconds, 0.1 to 999.9 minutes, or 0.1 to 999.9 hours for plugging in the housing 10, the first being preferred in seconds. Electrical panel 23 is illustrated on the left side of the sampler 10. Carrying handles 27a and 27b are screwed on the top of the sampler 10.

Lights 29a-29f, FIG. 2, indicate which sample bottle is being filled.

FIG. 3, a sectional view at 3—3 on FIG. 2, illustrates the third timer, purge timer 19 on the electrical panel 23. Stepping switch 16 with its accompanying rectifier 24 is mounted to control panel 23 and thus interconnected to the other two timers for operating as described above (interconnections not shown). FIG. 3 likewise shows brackets 25b and 25c for supporting their respective sample bottles 12b and 12c behind which are mounted solenoid valves, one valve each, connected to each bottle, valve 14b being illustrated as mounted to a base plate 26 in housing 11 for filling sample bottle 12b.

FIG. 4, a sectional view at 4—4 on FIG. 2, illustrates sample bottle 12b mounted in the housing 11 with bracket 25b. Solenoid valve 14b is shown mounted to base plate 26 in the housing 11 for being connected to its sample bottle 12b for precisely controlling the filling thereof. An important feature of the invention is that a valve 14b, for example, is responsive to the three timers, 17, 18, and 19. The pressure as well as the volume in the main line 20 from the well being sampled, well 21 for example, is maintained constant in the housing 11 with pressure regulator valve 30 despite any variations in fluid pressures from the well. Thus the valve is controlled by the timers to close only after the precise amount of well fluid has passed through the valve into the sample bottle.

While only six sample bottles are illustrated, obviously any suitable number may be utilized.

Briefly in operation, after the well fluid supply lines 20 and 22, FIG. 1, are connected to the automatic sampler 10, activation of the main power switch 28, FIG. 2 is accomplished, and the supply line 20 from the well is purged by purging timer operating purging solenoid valve 15 responsive to interval time 17. The desired interval of time is programmed into the interval timer and it signals the sampling timer 18 for beginning to fill the first sample bottle 12a simultaneously with closing of the purging valve 15. When the first sample bottle 12a is filled and the inlet valve 14a closed, the interval timer 17 delays for its preset time before activating the purging timer 19 for operating the purging valve 15. Then the interval timer 17 indexes the stepping switch 16 one position forward to permit the next or appropriate sample bottle 12b to be filled at the end of the purging cycle. After the proper time delay, the sampling timer 18 activates the next or appropriate solenoid valve 14b for filling sample bottle 12b while simultaneously closing the purging valve 15. Upon precise filling of the second sample bottle 12b, sample timer 18 controls the precise filling of the second sample bottle 12b through solenoid valve mechanism 14b. The instant this second bottle is filled, then interval timer 17 is activated to start on the next timing cycle. This automatic cycling is repeated until the sampler 10 is manually shut down with the main power switch 28.

Accordingly precise filling or measuring of each sample results in the least amount of sample to dispose of that may damage the environment, an important feature of the invention.

Instead of filling the sample bottles in numerical, consecutive order of 12a to 12f, the stepping switch may be preset to another prearranged order other than consecutive order for industrial security purposes, another feature of the invention.

Thus, each of the three interval, sample, and purging timers, 17-19, and the stepping switch 16 may be adjusted or varied for ease of adjustment of various portions of the whole cycle, another feature of the invention.

From the above, accurate timing results in obtaining the periodic samples of a multi-phase fluid product containing chemical species, for example, whose production changes with time, and chemical analysis of the samples provides reservoir description. The arrival of various chemicals in production wells from injection wells may indicate the speed of travel through the formation among other characteristics.

Accordingly, it will be seen that the disclosed methods of sampling a fluid from a well will operate in a manner which meets each of the objects set forth hereinbefore.

While only a few methods of the invention and one mechanism for carrying out the methods have been disclosed, it will be evident that various other methods and modifications are possible in the arrangement and construction of the disclosed methods and fluid sampling system without departing from the scope of the invention and it is accordingly desired to comprehend within the purview of this invention such modifications as may be considered to fall within the scope of the appended claims.

We claim:

1. A method for sampling a multi-phase fluid from a producing well comprising the steps of,
    (a) injecting a sample of the fluid from the well through a plurality of inlet valves on a plurality of fluid sample containers,
    (b) controlling the flow of the well fluids responsive to a switch means through the valves into the fluid sample containers to be filled periodically in consecutive order, one after the other, from the well for providing an improved method that is more accurate and more precise whereby smaller samples may be utilized and thus less waste well fluid is discharged that may damage the environment from the single well, and
    (c) flowing a multi-phase fluid product containing chemical species repeatedly from the producing well through a plurality of solenoid valves on the fluid sample containers into the fluid sample containers for detecting the change with time of the chemical concentrations of the flowing multi-phase fluid product after arriving at the producing well from an injection well whereby analysis of the sample provides reservoir description and for improved accuracy and precision of operation of the well fluid sampler.

2. A method for sampling a multi-phase fluid from a well comprising the steps of,
    (a) flowing the multi-phase fluid from the well through a plurality of solenoid valves on a plurality of fluid sample containers,
    (b) controlling the flow of the multi-phase well fluid through the solenoid valves into the fluid sample containers, responsive to a stepping switch means, to be filled periodically from the well in consecutive order for providing an improved method for sampling well fluids that is more accurate and more precise, and
    (c) injecting the multi-phase fluid from the well through the solenoid valves responsive to the stepping switch means into different sample containers periodically, from the well in a different prearranged order other than numerical consecutive order for security purposes.

* * * * *